United States Patent [19]

Konz

[11] 4,035,178

[45] July 12, 1977

[54] HERBICIDAL 1,3-DIOXANES

[75] Inventor: Marvin Joseph Konz, Lockport, N.Y.

[73] Assignee: FMC Corporation, Philadelphia, Pa.

[21] Appl. No.: 719,311

[22] Filed: Aug. 31, 1976

[51] Int. Cl.² .................. A01N 9/28; C07D 319/06
[52] U.S. Cl. .................................. 71/88; 260/340.3;
260/340.5; 260/340.7; 260/340.9; 260/348 C;
260/348.5 L; 260/617 R; 260/632 R; 260/635 H
[58] Field of Search ..................... 260/340.7; 71/88

[56] References Cited

FOREIGN PATENT DOCUMENTS 2,243,685   3/1973   Germany ................. 260/340.7

*Primary Examiner*—Ethel G. Love
*Attorney, Agent, or Firm*—Harrison H. Young, Jr.; Henry R. Ertelt

[57] ABSTRACT

A new class of herbicidal compounds consisting of 1,3-dioxanes carrying substituents other than hydrogen in the 2-, 4-, 5-, and 6-positions of the dioxane ring exhibits preemergence and postemergence herbicidal activity, controlling effectively the growth of selected grassy species. The synthesis of members of this class is described in detail, and the utility of representative compounds is exemplified.

13 Claims, No Drawings

HERBICIDAL 1,3-DIOXANES

This invention describes novel herbicidal compounds, new herbicidal compositions, and new methods for preventing and destroying undesired plant growth by preemergence and postemergence application of said new and useful herbicidal compositions to the locus where control is desired. Effective control of the growth of a variety of grassy plant species is obtained. At levels of preemergence application which prevent growth of grasses, the compounds of the invention show selectivity favorable to soybeans, cotton, wheat, sugarbeets, tomato, and peanuts. The herbicidal compositions may be applied and utilized by commonly accepted methods.

Herbicidal 1,3-dioxanes carrying substitutents other than hydrogen in the 2- and 5-positions of the dioxane ring have been described in the patent literature, for example in U.S. Pat. No. 3,753,678 Aug. 21, 1973) and in British Pat. No. 1,293,546 Oct. 18, 1972). The substituted 1,3-dioxanes of the prior art may be obtained by reacting an arylmethyl chloride or bromide with a 2-substituted-5-hydroxy-1,3-dioxane; copending application Ser. No. 541,386, of common assignee with U.S. Pat. No. 3,753,678, discloses a stereospecific process for the preferred stereoisomers of the 2-substituted-5-hydroxy-1,3-dioxanes and of the herbicidal 2-substituted-5-benzyloxy-1,3-dioxanes. The 2-substituted-5-hydroxy-1,3-dioxanes have commonly been obtained by acetalization of a carbonyl compound, an aldehyde, for example, with glycerol or a 2-alkyl glycerol. The carbon in the 5-position of the dioxane will thus carry hydrogen of alkyl (which may be optionally substituted with halogen) in addition to a hydroxy group or arylmethoxy group (benzyloxy, for example). In the previously disclosed 1,3-dioxanes, the carbons in the 4-position and the 6-position carried only hydrogen.

It has been found that by introducing a substituent, for example a lower alkyl group, in the 4-position or in the 4- and the 6-positions of the previously known herbicidal 1,3-dioxanes, herbicidal activity is retained and may be enhanced. The new class of 1,3-dioxanes substituted in the 4-position has shown an unexpected increase in herbicidal activity over the prior art dioxanes with no substitution in the 4-position. Thus in one aspect of the invention, novel herbicidal compounds contain a 1,3-dioxane ring having the following classes of substituents: on the 2-position, a lower alkyl group (1 to 4 carbon atoms); on the 4-position, a lower alkyl group (1 to 8 carbon atoms) or a phenyl group; on the 5-position, a benzyloxy group which may carry one or two chlorine, fluorine, or methyl groups on the phenyl nucleus of the benzyloxy group. It is contemplated that the substituent in the 2-position of the dioxane may also be halogenated alkyl, cyanoalkyl, aryl, arylalkyl, aryloxyalkyl, cycloalkyl, arylalkoxyalkyl, alkoxyalkyl, alkenyl (including substituted alkenyl), alkynyl, alkylthioalkyl, alkylsulfinylalkyl or alkylsulfonylalkyl, where any aryl radical is phenyl, furyl, or thienyl which is unsubstituted or carries a single X substituent, such as fluorine, chlorine, bromine, lower alkyl or lower alkoxy. It is contemplated that the substituent in the 5-position may also be furylmethoxy, thienylmethoxy, or 2-pyridylmethoxy, of which the heteronucleus may be substituted as is the phenyl nucleus of a 5-benzyloxy group. It is contemplated that the substituent in the 4-position may also be halogenated alkyl, cyanoalkyl, arylalkyl, cycloalkyl, alkoxyalkyl. It is contemplated also that the 5-position may carry a second group consisting of lower alkyl or lower haloalkyl, and that a divalent polymethylene radical may join the 5-position and the 4-position, thereby forming a cycloalkyl ring condensed with the 1,3-dioxane.

One group of herbicidal compounds in accordance with this invention has the following formula (in which the numbering of the R-substituent signals the numbering of the positions on the 1,3-dioxane ring:

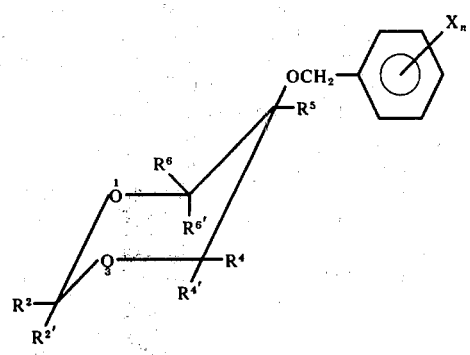

wherein $R_2$ is alkyl of 1 to 4 carbon atoms and $R^{2'}$ is hydrogen; $R^4$ is alkyl of 1 to 4 carbon atoms and $R^{4'}$ is hydrogen; $R^5$ is hydrogen or alkyl of 1 to 4 carbon atoms; $R^6$ is hydrogen or alkyl of 1 to 4 carbon atoms and $R^{6'}$ is hydrogen; X is chloro, fluoro, or methyl; and $n$ is 0, 1, or 2.

In preferred compounds of this general formula, $R^2$ is methyl, ethyl, propyl, isopropyl, and tert-butyl; $R^4$ is methyl, ethyl, propyl, isopropyl, and tert-butyl, $n$ is 0 or 1 and X is chloro or methyl in the 2-position of the phenyl ring.

It is seen that while $R^{4'}$ and $R^{6'}$ will always be hydrogen, and $R^4$ will always be alkyl, $R^5$ and $R^6$ may each be independently hydrogen or alkyl. This is seen to give rise to four possible combinations, as follows:

|     | $R^4$ | $R^5$ | $R^6$ | Theoretical No. Stereoisomers |
|-----|-------|-------|-------|-------------------------------|
| (a) | alkyl | H     | H     | 4                             |
| (b) | alkyl | alkyl | H     | 4                             |
| (c) | alkyl | H     | alkyl | 6                             |
| (d) | alkyl | alkyl | alkyl | 6                             |

When $R^2$ is taken as a reference group, the benzyloxy group in the 5-position may be oriented axially (cis) or equatorially (trans). When $R^4$ and $R^6$ are alkyl they may also be oriented axially or equatorially to the reference group. The number of conceivable stereoisomers is substantially greater than the number of possible substitutions. For (a) above there are four conceivable stereoisomers, for (b) there are four conceivable stereoisomers, for (c) there are six conceivable stereoisomers, and for (d) there are six conceivable stereoisomers. Although there are 20 conceivable stereoisomers among the four substitution isomers (a), (b), (c), and (d), not all will be obtainable because of spatial restrictions or equilibria favoring an alternate orientation.

Optical isomers are also possible, as there are asymmetric centers in the dioxane molecules.

Herbicidally preferred are compounds in which the 5-benzyloxy group bears a cis-relationship to the 2-substituent. Expecially preferred herbicidally are compounds in which the 4-substituent and the 5-benyloxy group both bear a cis-relationship to the 2-substituent.

The stereochemistry of the derviatives of 5-hydroxy-1,3-dioxane has been discussed in the scientific literature [see, for example, Baggett et al, J. Chem. Soc. 2574(1960) and Dobinson and Foster, J. Chem. Soc. 2338(1961)]. As pointed out there, a cis-relationship between the 5-substituent and the 2-substituent occurs when the 5-substituent is in an axial position and the 2-substituent is in a equatorial position. Much information concerning the structures involved can be obtained from nuclear magnetic resonance spectra, U.S. Pat. No. 3,753,678 contains a discussion of nmr analysis of 2,5-dialkyl-5-hydroxy-1,3-dioxanes. [See also, Gelas, Bull. Soc. Chim. France 1975 (5–6) 1237–1242, for a discussion of nmr analysis of an isomeric mixture of 2,4-dimethyl-5-hydroxy-1,3-dioxanes.]

Preparation of the compounds of the invention and of intermediates from which they are prepared is described below. In the descriptions which follow, all temperatures are in degrees centigrade. All reduced pressures not otherwise designated are pressures normally attainable using a water aspirator.

The isomerization of hydroxylated dioxolanes and dioxanes by selective distillation in acid medium has been described by J. Gelas, Bull. Soc. Chim. France 1970 (11), 4041–4046. This method has been used to prepare an alcohol precursor to the compounds of this invention, r-2-ethyl-c-5-hydroxy-c-4-methyl-1,3-dioxane. Gelas (at Bull. Soc. Chim. France 1975 (5–6) 1228–1236) has described the synthesis of a mixture of erythro and threo 1,2,3-butanetroils from a mixture of cis and trans crotyl alcohols, and its subsequent reaction with acetaldehyde to give an isomertic mixture of dioxolanes and 2,4-dimethyl-5-hydroxy-1,3-dioxanes. These reactions are set forth in the following schema:

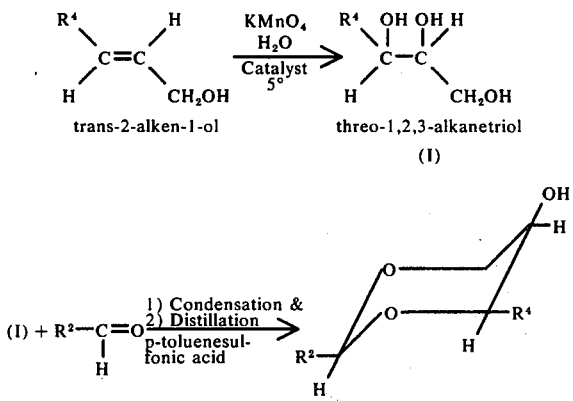

SYNTHESIS OF INTERMEDIATES

A'. threo-1,2,3-Butanetroil

A stirred mixture of 12.5 of trans-2-buten-1-ol and 0.5 g. of 2,3,11,12-dicyclohexyl-1,4,7,10,13,16-hexaoxacyclooctadecane ("dicyclohexyl-18-crown-6") in 125 ml of water was cooled to 5° and maintained near 5° for one-half hour during addition of 32.88 go of potassium permanganate. Upon completion of the addition the temperature of the mixture was allowed to rise to ambient temperature, at which the mixture was stirred for 2.5 hours. The reaction mixture was filtered and the filtrate was evaporated under reduced pressure until a viscous liquid residue remained. The residue was distilled using a short-path distillation system, yielding 6.13 g of clear, viscous threo-1,2,3-butanetriol; bp 97–99°/0.02–0.025 mm. The ir and nmr spectra was consistent with the assigned structure.

Analyses calc'd for $C_4H_{10}O_3$; C 45.27; H 9.50.
Found: C 45.54; H 9.58.

A. r-2-Ethyl-c-5-hydroxy-c-4-methyl-1,3-dioxane

A solution of 23.26 g of propionaldehyde, 42.56 g of threo-1,2,3-butanetriol, and 0.93 g of p-toluenesulfonic acid in 750 ml of hexane was stirred at ambient temperature for 1 to 2 hours, and maintained at reflux temperature for 16 hours, by which time 6.40 ml of water had been azeotropically distilled from the mixture (of a total of 7.23 ml, theoretically obtainable by acetalization with the triol). The reaction mixture was cooled to ambient temperature and an additional 3.0 g of propionaldehyde was added, and the mixture was heated under reflux for two hours, during which the remainder of the expected water was azeotropically distilled. The reaction mixture was cooled and washed with three 75-ml portions of saturated sodium bicarbonate solution and four 75-ml portions of saturated sodium chloride solution. The organic layer was dried with sodium sulfate and filtered; and the filtrate was evaporated under reduced pressure, yielding 34.76 g of yellow liquid. The sodium bicarbonate and sodium chloride wash solutions were extracted thrice with 200-ml portions of diethyl ether, and the combined ether layers were washed twice with 75-ml portions of saturated sodium chloride solution, dried with sodium, sulfate, and filtered. The filtrate was evaporated under reduced pressure, yielding 22.88 g of yellow liquid. The two portions of yellow liquid were analyzed by gas chromatography and were found to resemble each other. They were combined, mixed with 0.93 g of p-toluenesulfonic acid and distilled under reduced pressure. Six fractions (A to F) were collected and analyzed by gas chromatography. Fraction F and the pot residue were combined and further distilled, yielding four fractions (G,H,I,J) which were analyzed by gas chromatography also. A sample of fraction D was submitted for elemental analysis.

Analyses calc'd for $C_7H_{14}O_3$: C 57.51; H 9.65.
Found: C 57.80; H 9.94.

Fractions C, D, E, G, and H were combined to give 31.36 g of r-2-ethyl-c-5-hydroxy-c-4-methyl-1,3-dioxane; bp 79–81°/15–17 mm.

B. c-5-Hydroxy-r-2-isopropyl-c-4-methyl-1,3-dioxane

This compound was prepared in the manner of the 2-ethyl compound (A), using 45.6 g of isobutyraldehyde (instead of propionaldehyde) and 66.2 g of butanetriol. The reaction mixture was distilled under reduced pressure. The yield was 62.0 g of c-5-hydroxy-r-2-isopropyl-c-4-methyl-1,3-dioxane; bp 72–75°/12 mm. The nmr spectrum was consistent with the proposed structure.

Analyses calc'd for $C_8H_{16}O_3$: C 59.98; H 10.07.
Found: C 60.13; H 10.11.

C'. threo-1,2,3-Hexanetroil

This compound was prepared in the manner of the butanetroil (A') using 125.00 g of trans-2-hexen-1-ol, 236.60 g of potassium permanganate, and 4.65 g of dicyclohexyl-18-crown-6in 1500 ml of water. The crude product was distilled under pressure to give 26.4 g of threo-1,2,3-hexanetriol; bp 165°–175° (pressure too low to record).

C. r-2-Ethyl-c-5-hydroxy-c-4-propyl-1,3-dioxane

This compound was prepared in the manner of the previous 2-ethyl compound (A), using 26.4 g of threo-1,2,3-hexanetriol, 11.44 g of propionaldehyde, and 0.58 g of p-toluenesulfonic acid in 170 ml distilled hexane. The crude product was distilled to give 14.3 g of r-2-ethyl-c-5-hydroxy-c-4-propyl-1,3-dioxanne; bp 34°/0.025 mm. The nmr and ir spectra were consistent with the assigned structure.

Analyses calc'd for $C_9H_{18}O_3$: C 62.04; H 10.41.
Found: C 61.87; H 10.68.

Using parallel methods, starting with the appropriate alkanetriol and aldehyde, there is also prepared: D. r-2-ethyl-c-5-hydroxy-c-4-isopropyl-1,3-dioxane, bp 42.5°–45°/0.35–0.4 mm; E. c-5-hydroxy-r-2-c-4-dimethyl-1,3-dioxane, bp 54–55°/3.75 mm; F. c-5-hydroxy-c-4-methyl-r-2-propyl-1,3-dioxane, bp 45/0.5 mm; and G. r-2-tert-butyl-c-5-hydroxy-c-4-methyl-1,3-dioxane, mp 53.5°–54.5°.

H′. erythro-1,2,3-Butanetriol

To a stirred mixture of 100 g of crotyl alcohol in 900 ml of p-dioxane and 450 ml of water was gradually added 188.7 g of 30% hydrogen peroxide (56.6 g $H_2O_2$); this was followed by the addition of 2.82 g of tungstic oxide ($WO_3$) catalyst. Upon completion of the addition the reaction mixture was stirred at ambient temperature for 1 hour, at 35° for 16 hours, at 45° for 8 hours, than at 40° for 16 hours. The reaction mixture was cooled to ambient temperature and tested with potassium iodide paper for excess peroxide; the test was negative. The reaction mixture was filtered through a Celite diatomaceous earth filter to remove catalyst. The filtrate was neutralized with aqueous 2N sodium hydroxide, and evaporated under reduced pressure to a residue. The residue was taken up in 800 ml of methanol and dried with sodium sulfate and magnesium sulfate. The mixture was filtered through a Celite diatomaceous earth filter and the filtrate evaporated under reduced pressure to a residue. The residue was distilled using a shortpath distilling system to give 110.75 g of erythro1,2,3-butanetriol; bp 97°/0.03 mm.

Analyses calc'd for $C_4H_{10}O_3$: C 45.27; H 9.50.
Found: C 44.98; H 9.29.

H. r-2-Ethyl-t-5-hydroxy-c-4-methyl-1,3-dioxane

The dioxolane precursor to this compound was prepared in the manner of previous 5-hydroxy compounds, using 50.00 g of erythro-1,2,3-butanetriol, 27.4 g of propionaldehyde, and 0.75 g of p-toluenesulfonic acid in 255 ml of hexane. The crude reaction mixture was distilled in nineteen fractions to give a mixture of dioxolanes; bp 58°–76.8°/2.15-3.40 mm. Fractions 3–15 were combined and redistilled in four fractions to give a mixture of dioxolanes, predominately cis-2-ethyl-4-(erythro-1-hydroxyethyl)-1,3-dioxolane; bp 53°–67°/2.5 mm. A sample of 8.80 g of fraction four of this distillation (bp 67°/2.5 mm, 65.8% in cis-2-ethyl-4-(erythro-1-hydroxy-ethyl)-1,3-dioxolane by gas chromatographic analysis) was combined with 0.1 g of p-toluenesulfonic acid and placed in a refrigerator for 6 days, in an effort to cause equilibration to r-2-ethyl-t-5-hydroxy-c-4-methyl-1,3-dioxane. After this time the 8.80 g sample was taken up in 150 ml of diethyl ether. The ether layer was washed with three portions of 50 ml each of an aqueous solution saturated with sodium bicarbonate, then with three portions of 50 ml each of an aqueous solution saturated with sodium chloride. The ether layer was dried with sodium sulfate and filtered. The filtrate was evaporated under reduced pressure to a residue that was 86.8% in r-2-ethyl-t-5-hydroxy-c-4-methyl-1,3-dioxane (by gas chromatographic analysis). The crude residue was distilled in five fractions to give a mixture of dioxolanes and dioxanes; bp 87°–104°/18–20 mm. It was felt that a trace of acid in the distillation vessel caused re-equilibration. The fractions were combined and 0.1 g of p-toluenesulfonic acid was added. Equilibration took place in a refrigerator during 8 days. After this time the equilibration mixture was taken up in 150 ml of diethyl ether and washed with three portions of 50 ml each of an aqueous solution saturated with potassium carbonate, then three portions of 25 ml each of an aqueous solution saturated with sodium chloride. The ether layer was dried with sodium sulfate and filtered. The filtrate was evaporated under reduced pressure to a residue of 8.65 g that was 82.7% (GC analysis) in r-2-ethyl-t-5-hydroxy-c-4-methyl-1,3-dioxane. The crude residue was distilled from a vessel containing 0.05 g of sodium hydroxide using a spinning band distilling system to obtain 15 fractions, bp 87°–101°/12–13 mm. Fractions 9–15 were combined to give 2.48 g of r-2-ethyl-t-5-hydroxy-c-4-methyl-1,3-dioxane; bp 100°–101°/12–13 mm, 93–95% pure by gas chromatographic analysis. The nmr spectrum was consistent with the assigned structure.

Analyses calc'd for $C_7H_{14}O_3$: C 57.51; H 9.65.
Found: C 57.42; H 9.90.

J′. Mixture of erythro- and threo-3-Methyl-2,3,4-pentanetriol

A mixture of 75.4 g of 3-methyl-penten-2-ol and 91.44 g of 35% hydrogen peroxide (32.00 g $H_2O_2$) in 500 ml of water was stirred for 1 hour during addition of 1.8 g of tungstic oxide ($WO_3$) catalyst. The mixture was maintained at reflux temperature for approximately 48 hours. It was tested for unreacted hydrogen peroxide, and the excess was removed with 6.30 g sodium sulfite in 50 ml water. The solution was filtered, and concentrated under reduced pressure to a residual 62.9 g of reddish-yellow dispersion of solid in viscous liquid. The material was dissolved in methanol and the solution filtered. The filtrate was concentrated under reduced pressure to a residual 60.45 g of dark brown viscous liquid. Due to the viscosity of the liquid, stable pressures were difficult to obtain, however 35.0 g of erythro- and threo-3-methyl-2,3,4-pentanetriol, bp 85°–90°/.09-.12 mm were collected.

J. r-2-Ethyl-c-5-hydroxy-t-4, t-5, c-6-trimethyl-1,3-dioxane and r-2-ethyl-t-5-hydroxy-c-4, c-5, c-6-trimethyl-1,3-dioxane in mixture with dioxolanes This mixture was prepared in the manner of previous hydroxydioxanes, using 35.0 g of a mixture of erythro- and threo-3-methyl-2,3,4-pentanetriol, 15.14 g of propionaldehyde, and 0.49 g of p-toluenesulfonic acid in 200 ml of hexane. The crude reaction mixture was distilled (distillation A) under reduced pressure, using a spinning band distilling column, to give in eight fractions 37.3 g of distillate; bp 30°–65°/2.75-3.30 mm. Each fraction was subjected to gas chromatographic analysis; and fractions were found to be mixtures of cis- and trans-hydroxy-1,3-dioxanes and dioxolanes.

Fractions 1-4, bp 49.5°–65°/2.90–3.30 mm, were combined and redistilled (distillation B) in six fractions to give 14.1 g of distillate; bp 35°–56.5°/2.80–3.05 mm. Gas chromatographic anaylsis of each fraction indicated fractions 1-4 were predominately cis-hydroxy-1,3-dioxane and dioxolane, and fractions 5,6 and the distillation vessel residue were predominately trans-hydroxy-1,3-dioxane and dioxolane. Fraction 4, bp 35°–55°/2.95–3.00 mm, was redistilled (distillation C) to give an analytical sample of cis-hydroxy-1,3-dioxane and dioxolane. Analyses calc'd for $C_9H_{18}O_3$: C 62.04; H 10.41.

Found: C 62.29; H 10.70.

Fractions 1,5,6, and the distillation vessel residue from distillation B and Fractions 5–8 from distillation A were combined and redistilled (distillation D) in 10 fractions to give 27.3 g of distillate bp 35°–65°/2.9–3.1 mm. Fraction 2, by gas chromatographic analysis, was 88.1% r-2-ethyl-c-5-hydroxy, t-4, t-5, c-6-trimethyl-1,3-dioxane and what is believed to be 2-ethyl-4,5-dimethyl-4-(1-hydroxyethyl)-1,3-dioxolane; bp 45°–49°/3.0 mm. The weight of this fraction was 5.56 g.

K" 2-[(1-Hydroxy-1-methyl)ethyl]-2-methyl-oxirane

A solution of 46.7 g of 2,3-dimethyl-3-buten-2-ol in 602 ml of chloroform was cooled to 0°–5° in a dry ice-acetone bath. To this was added dropwise, during 4 hours, a solution of 96.5 g of m-chloroperoxybenzoic acid (113.5 g of 85%) in 966 ml of chloroform. The reaction mixture temperature was maintained at 0°–5° throughout the addition. Upon complete addition, the reaction mixture was allowed to warm to ambient temperature where it was stirred for 18 hours. To the reaction mixture was slowly added a solution of 11.8 g of sodium sulfite in a minimum amount of water. The reaction mixture was tested for peroxides using wet acidic sodium iodide-starch paper; there were no peroxides present. Concentration of the reaction mixture to below one-half the original volume resulted in precipitation of benzoic acid from the reaction mixture. The benzoic acid was removed by filtration. The concentration, precipitation, and filtration was repeated several time until at the last concentration only a small amount of precipitated benzoic acid was collected. There remained 16.6 g of residual yellow liquid, from which on standing a white solid crystallized. The liquid portion was decanted off and the solid was washed with diethyl ether. The ether wash was added to the liquid portion. The white solid had a melting point of 116°–118° and decomposed explosively at 170°–180°. The liquid portion was distilled using a Vigreux column, to give 9.32 g of 2-[(1-hydroxy-1- methyl)ethyl]-2-methyloxirane bp 35°–65°/15-20 mm. The nmr spectrum was consistent with the assigned structure.

K' 2,3-Dimethyl-1,2,3-butanetriol

A mixture of 8.73 g of 2-[(1-hydroxy-1-methyl)ethyl]-2-methyloxirane, 7 drops of concentrated sulfuric acid, 15 ml of p-dioxane, and 100 ml of water was heated at 55° C during 16 hours. The reaction mixture was made neutral to phenolphthalein indicator, using sodium hydroxide solution. The mixture was evaporated under reduced pressure to a viscous cloudly liquid. The liquid was dissolved in ethanol and filtered. The filtrate was evaporated under reduced pressure to give 9.82 g of viscous residual oil. The oil was distilled, using a short-path distilling column, to give 8.16 g of 2,3-dimethyl-1,2,3-butanetriol; bp 85°–94°/0.2 mm. The nmr spectrum was consistent with the assigned structure.

K.

r-2-Ethyl-c-5-hydroxy-c-4,t-4,t-5-trimethyl-1,3-dioxane

This compound was prepared in the manner of previous hydroxydioxanes, using 7.76 g of 2,3-dimethyl-1,2,3-butanetriol, 3.35 g of propionaldehyde, and 0.13 g of p-toluenesulfonic acid in 100 ml of hexane. The crude product was distilled under reduced pressure to give 2.12 g of r-2-ethyl-c-5-hydroxy-c-4,t-4,t-5-trimethyl-1,3-dioxane; bp 60.5°–62.5°/1.0–3.5 mm. The nmr spectrum was consistent with the assigned structure.

Analyses calc'd for $C_9H_{18}O_3$: C 62.04; H 10.41.

Found: C 61.75; H 10.49.

L". 1-Cyclohexenemethanol

To a rapidly stirred mixture of 18.2 g of lithium aluminum hydride in 1000 ml of dried diethyl ether, at ambient temperature, was added dropwise 50.5 g of 1-cyclohexenecarboxylic acid. After complete addition the reaction mixture was stirred at ambient temperature for 1 hour. The reaction mixture was then heated under reflux for 4 hours. After the period of reflux, approximately 40 ml of water was added dropwise to decompose the excess lithium aluminum hydride; this was followed by addition of approximately 100 ml of an aqueous solution saturated with sodium sulfate. The reaction mixture was filtered and the filtrate washed with three portions of 100 ml each of an aqueous solution saturated with sodium chloride. The diethyl ether layer was dried with anhydrous sodium sulfate and filtered. The filtrate was evaporated under reduced pressure to a residue. The residue was distilled using a Vigreux column to give 37.3 g of 1-cyclohexenemethanol; bp 101°–102°/28–30 mm.

L'. 1,2-Dihydroxycyclohexanemethanol

A solution of 24.9 g of potassium permanganate and 18.7 g of magnesium sulfate in 498 ml of water was added dropwise during 1.5 hours to a solution of 22.23 g of 1-cyclohexenemethanol in 373 ml of ethanol. During the dropwise addition, the reaction mixture temperature was maintained at 15°–20°. The reaction mixture was filtered to remove the by-product manganese dioxide. The filtrate was evaporated under reduced pressure to a residual oil. The residual oil was taken up in ethanol and dried with magnesium sulfate. The mixture was filtered and the filtrate evaporated under reduced pressure to a residual oil. The residual oil was distilled using a short-path distilling system to give 6.44 g of 1,2-dihydroxycyclohexanemethanol; bp 124°–125°/0.025 mm.

L. (2α, 4aα, 8aβ)-2-Ethylhexahydro-4a-hydroxy-4H-1,3-benzodioxin

This compound was prepared as were previous 5-hydroxy compounds, using 2.56 g of propionaldehyde, 6.44 g of 1,2-dihydroxycyclohexanemethanol, and 0.40 g of p-toluenesulfonic acid in 100 ml of hexane. The crude product was distilled using a short-path distilling system, to give 6.80 g of (2α, 4aα, 8aβ)-2-ethylhexahydro-4a-hydroxy-4H-1,3-benzodioxin; bp 81°–100°/1.0 mm. The nmr spectrum was consistent with the assigned structure.

M''. 1,2-Epoxycyclohexamethanol

A stirred solution of 1-cyclohexemethanol in 220 ml of chloroform was cooled to 0°–5° and 35.9 g of m-chloroperoxybenzoic acid (41.6 g of 85% pure material) in 355 ml of chloroform was added dropwise during three hours. The temperature of the reaction mixture was maintained at 0°–5° throughout the addition. Upon completion of the addition the reaction mixture was allowed to warm to ambient temperature during 24 hours. The reaction mixture was evaporated under reduced pressure to one-half the original volume and filtered. The filtrate was washed with three portions of 150 ml each of an aqueous solution saturated with sodium bicarbonate; then with three portions of 150 ml each of an aqueous solution saturated with sodium chloride. The chloroform layer was dried with sodium sulfate and filtered. The filtrate was evaporated under reduced pressure to a residue. The residue was distilled using a Vigreux column to give 10.8 g of 1,2-epoxycyclohexanemethanol; bp 51°–52°/0.08-0.085 mm; $n_D^{25}$=1.4738. The nmr and the ir spectra were consistent with the assigned structure.

M'. 1,2-Dihydroxycyclohexanemethanol

A stirred mixture of 10.6 g of 1,2-epoxycyclohexanemethanol and 8 drops of concentrated sulfuric acid in 100 ml of p-dioxane and 100 ml of water was heated at 60°–70° for 18 hours. The reaction mixture was neutralized with sodium hydroxide, and evaporated under reduced pressure to a viscous residue. The residue was taken up in methanol and dried with sodium sulfate. The mixture was filtered and the filtrate evaporated under reduced pressure to a residue. The residue was distilled to give 10.8 g of 1,2-dihydroxycyclohexanemethanol; bp 170°–240°/0.02 mm. The nmr spectrum was consistent with the assigned structure.

M. ($2\alpha$, $4a\beta$, $8a\beta$)-2-Ethylhexahydro-4a-hydroxy-4H-1,3-benzodioxin This compound was prepared as were previous 5-hydroxy compounds, using 4.21 g of propionaldehyde, 10.60 g of 1,2-dihydroxycyclohexanemethanol, and 0.65 g of p-toluenesulfonic acid in 166 ml of hexane. The crude reaction mixture was distilled to give 8.75 g of ($2\alpha,4a\beta$, $8a\beta$)-2-ethylhexahydro-4a-hydroxy-4H-1,3-benzodioxin that was approximately 80–85% pure; bp 64.5°–67°/0.01 mm.

The 8.75 g of product and 1.85 g obtained from another preparation were combined and subjected to selective benzoylation to remove dioxolane alcohols believed to be present as impurities in the 1,3-benzodioxin, proceeding as follows: To a solution of 10.60 g of the 1,3-benzodioxin in 50 ml of pyridine were added dropwise, during 0.5 hour, 9.78 g of benzoyl chloride. The addition was done at ambient temperature. Upon completion of the addition the reaction mixture was stirred at ambient temperature for 16 hours. The reaction mixture was evaporated under reduced pressure to a residual oil. The residue was poured into 150 ml of cold water and extracted with three portions of 100 ml each of diethyl ether. The combined ether layers were washed with three portions of 100 ml each of cold water; three portions of 100 ml each of an aqueous solution 2% in hydrogen chloride; three portions of 100 ml each of an aqueous solution saturated with sodium bicarbonate; and three portions of 100 ml each of cold water. The ether layer was dried with sodium sulfate and filtered. The filtrate was evaporated under reduced pressure to a residual oil. The residual oil was distilled using a Vigreux column to give 4.95 g of 97.6% pure ($2\alpha$, $4a\beta$, $8a\beta$)-2-ethylhexahydro-4a-hydroxy-2H-1,3-benzodioxin; bp 70°–71°/0.25 mm. The nmr and the ir spectra were consistent with the assigned structure.

Analyses calc'd for $C_{10}H_{18}O_3$: C 64.49; H 9.74.
Found: C 64.62; H 9.49.

EXAMPLE I r-2-Ethyl-c-5-(2-fluorobenzyloxy)-c-4-methyl-1,3-dioxane

A 2.53-gram portion of a suspension of sodium hydride in mineral oil (1:1 by weight) was placed in a reaction vessel and washed with two 50-ml portions of dry hexane and two 50-ml portions of dry toluene. One hundred ml of dry toluene was added to the sodium hydride and stirred while 7.00 g of r-2-ethyl-c-5-hydroxy-c-4-methyl-1,3-dioxane was added dropwise, which required 15 minutes, during which the exothermic reaction raised the temperature of the reaction mixture from 23° to 33°. The reaction mixture was heated under reflux for 5.5 hours, and cooled to ambient temperature, at which 7.62 g of 2-fluorobenzyl chloride was added during 5 minutes. The reaction mixture was heated under reflux for 18 hours. The reaction mixture was washed with three 50-ml portions of cold water (until washwater showed approximately pH 5). The organic layer was separated, dried with sodium sulfate, and filtered. The filtrate was concentrated under reduced pressure to a residual 11.87 g of yellow liquid, which was distilled under reduced pressure, yielding 7.85 g of r-2-ethyl-c-5-(2-fluorobenzyloxy)-c-4-methyl-1,3-dioxane; bp 95.5°–98°/0.05-0.075 mm; ir and nmr spectra were consistent with the assigned structure.

Analyses cal'd for $C_{14}H_{29}FO_3$: C 66.12; H 7.53.
Found: C 66.40; H 7.55.

EXAMPLE II r-2-Ethyl-c-4-methyl-c-5-(2-methylbenzyloxy)-1,3-dioxane

The procedure of Example I was followed, using 2.53 g of the sodium hydride-mineral oil suspension and 7.00 g of r-2-ethyl-c-5-hydroxy-c-4-methyl-1,3-dioxane, and 7.41 g of 2-methylbenzyl chloride instead of 2-fluoro-benzyl chloride. The washed, dried, and filtered reaction mixture was concentrated under reduced pressure to a residual 11.78 g of dark yellow liquid. This was purified by column chromatography, using a silica gel column eluted with high-boiling petroleum ether, and high-boiling petroleum ether:ethyl acetate (98:2) until 245 fractions were collected. Cuts 95–122 were combined and concentrated to yield 6.32 g of yellow liquid. The two portions were distilled under reduced pressure and the combined distillates comprised 6.90 g of r-2-ethyl-c-4-methyl-c-5-(2-methylbenzyloxy)-1,3-dioxane; bp 104°–106°/0.05-0.075 mm; ir and nmr spectra were consistent with the assigned structure.

Analyses calc'd for $C_{15}H_{22}O_3$: C 71.97; H 8.86.
Found: C 72.02; H 8.89.

EXAMPLE III c-5-(2-Chlorobenzyloxy)-r-2-ethyl-c-4-methyl-1,3,-dioxane

The procedure of Example I was followed, using 2.53 g of sodium hydride-mineral oil suspension and 7.00 g of r-2-ethyl-c-5-hydroxy-c-4-methyl-1,3-dioxane, and 8.48 g of 2-chlorobenzyl chloride instead of 2-fluorobenzyl chloride. The washed, dried, and filtered reaction mixture was concentrated under reduced pressure to a residual 12.96 g which was distilled under reduced pressure, yielding 7.46 g of c-5-(2-chlorobenzyloxy)-r-2-ethyl-c-4-methyl-1,3-dioxane; bp 110°–114°/0.32–0.40 mm; ir and nmr spectra were consistent with the assigned structure.

Analyses calc'd for $C_{14}H_{16}ClO_3$: C 62.10; H 7.07. Found: C 62.40; H 7.09.

EXAMPLE IV c-5-Benzyloxy-r-2-ethyl-c-4-methyl-1,3-dioxane

The procedure of Example I was followed, using 2.52 g of the sodium hydride-mineral oil suspension and 7.0 g of r-2-ethyl-c-5-hydroxy-c-4-methyl-1,3-dioxane, and 6.62 g of benzyl chloride instead of 2-fluorobenzyl chloride. After being heated at reflux 16 hours, the reaction mixture was washed with five 100-ml portions of water (until washwater showed approximately pH 5). The organic layer was separated, dried with sodium sulfate, and filtered. The filtrate was concentrated under reduced pressure to a residual 11.56 g, which was distilled under reduced pressure, yielding 6.57 g of c-5-benzyloxy-r-2-ethyl-c-4-methyl-1,3-dioxane; bp 110°–114°/0.01 mm; ir and nmr spectra were consistent with the assigned structure.

Analyses calc'd for $C_{14}H_{20}O_3$: C 71.15; H 8.53. Found: C 71.43; H 8.33.

EXAMPLE V c-5-Benzyloxy-r-2-isopropyl-c-4-methyl-1,3-dioxane

This compound was prepared in the manner of Example I, using 10.0 g c-5-hydroxy-r-2-isopropyl-c-4-methyl-1,3-dioxane, 8.7 g benzyl chloride, and 3.30 g of the suspension of sodium hydride in mineral oil (1:1 by weight). The reaction mixture was distilled under reduced pressure. The yield was 8.95 g of c-5-benzyloxy-r-2-isopropyl-c-4-methyl-1,3-dioxane; bp 110°–113°/0.020 mm. The ir and nmr spectra were consistent with the assigned structure.

Analyses calc'd for $C_{15}H_{22}O_3$: C 71.97; H 8.86. Found: C 72.20; H 8.57.

EXAMPLE VI c-5-(2-Fluorobenzyloxy)-r-2-isopropyl-c-4-methyl-1,3-dioxane

This compound was prepared in the manner of Example I, using 10.0 g c-5-hydroxy-r-2-isopropyl-c-4-methyl-1,3-dioxane, 9.92 g 2-fluorobenzyl chloride, and 3.30 g of the sodium-hydride:mineral oil (1:1). The reaction mixture was distilled under reduced pressure. The yield was 12.75 g of c-5-(2-fluorobenzyloxy)-r-2-isopropyl-c-4-methyl-1,3-dioxane; bp 103°–105°/0.020 mm. The ir and nmr spectra were consistent with the assigned structure.

Analyses calc'd for $C_{15}H_{21}FO_3$: C 67.14; H 7.89. Found: C 67.14; H 7.83.

EXAMPLE VII r-2-Isopropyl-c-4-methyl-c-5-(2-methylbenzyloxy)-1,3-dioxane

This compound was prepared in the manner of Example I, using 10.0 g c-5-hydroxy-r-2-isopropyl-c-4-methyl-1,3-dioxane and 9.64 g 2-methylbenzyl chloride. The reaction mixture was distilled under reduced pressure. The yield was 13.05 g of r-2-isopropyl-c-4-methyl-c-5-(2-methylbenzyloxy)-1,3-dioxane; bp 115°–117°/0.020 mm. The ir and nmr spectra were consistent with the assigned structure.

Analyses calc'd for $C_{16}H_{24}O_3$: C 72.69; H 9.15. Found: C 72.74; H 9.14.

EXAMPLE VIII c-5-(2-Chlorobenzyloxy)-r-2-isopropyl-c-4-methyl-1,3-dioxane

This compound was prepared in the manner of Example I, using 10.0 g c-5-hydroxy-r-2-isopropyl-c-4-methyl-1,3-dioxane and 11.0 g 2-chlorobenzyl chloride. The reaction mixture was distilled under reduced pressure. The yield was 8.13 g of c-5-(2-chlorobenzyloxy)-r-2-isopropyl-c-4-methyl-1,3-dioxane; bp 126°–130°/0.020 mm. The ir and nmr spectra were consistent with the assigned structure.

Analyses calc'd for $C_{15}H_{21}ClO_3$:; C 63.26; H 7.43. Found: C 62.96; H 7.25.

EXAMPLE IX c-5-Benzyloxy-r-2-ethyl-c-4-propyl-1,3-dioxane

This compound was prepared in the manner of Example I, using 3.0 g of r-2-ethyl-c-5-hydroxy-c-4-propyl-1,3-dioxane, 0.45 g of sodium hydride (0.90 g of a 50% dispersion of sodium hydride in mineral oil), and 2.39 g of benzyl chloride in 50 ml of dry toluene. The crude product was distilled under reduced pressure to give, in three fractions, 2.46 g of c-5-benzyloxy-r-2-ethyl-c-4-propyl-1,3-dioxane; bp 125°/0.01 mm. The nmr and the ir spectra were consistent with the assigned structure.

Analyses calc'd for $C_{16}H_{24}O_3$: C 72.69; H 9.15. Found: C 72.38; H 9.29.

EXAMPLE X r-2-Ethyl-c-5-(2-fluorobenzyloxy)-c-4-propyl-1,3-dioxane

This compound was prepared in the manner of Example I, using 2.40 g of r-2-ethyl-c-5-hydroxy-c-4-propyl-1,3-dioxane, 0.36 g of sodium hydride (0.72 g of a 50% dispersion of sodium hydride in mineral oil), and 2.21 g of 2-fluorobenzyl chloride in 50 ml of dried toluene. The crude product was distilled under reduced pressure to give, in three fractions, 1.79 g of r-2-ethyl-c-5-(2-fluorobenzyloxy)-c-4-propyl-1,3-dioxane; bp 140°/0.01 mm. The nmr and the ir spectra were consistent with the assigned structure.

Analyses calc'd for $C_{16}H_{23}FO_3$: C 68.06; H 8.57. Found: C 68.20; H 8.54.

EXAMPLE XI r-2-Ethyl-c-5-(2-methylbenzyloxy)-c-4-propyl-1,3-dioxane

This compound was prepared in the manner of Example I, using 6.00 g of r-2-ethyl-c-5-hydroxy-c-4-propyl-1,3-dioxane, 0.83 g of sodium hydride (1.67 g of a 50% dispersion of sodium hydride in mineral oil), and 4.88 g of 2-methylbenzyl chloride in 50 ml dried toluene. The crude product was distilled under reduced pressure to give, in three fractions, 7.00 g of r-2-ethyl-c-5-(2-methylbenzyloxy)-c-4-propyl-1,3-dioxane; bp 130°/0.010 mm. The nmr and the ir spectra were consistent with the assigned structure.

Analyses calc'd for $C_{17}H_{26}O_3$: C 73.34; H 9.41. Found: C 73.10; H 9.41.

EXAMPLE XII c-5-(2-Chlorobenzyloxy)-r-2-ethyl-c-4-propyl-1,3-dioxane

This compound was prepared in the manner of Example I, using 2.41 g of r-2-ethyl-c-5-hydroxy-c-4-propyl-1,3-dioxane, 0.36 g of sodium hydride (0.72 g of a 50% dispersion of sodium hydride in mineral oil) and 2.43 g of 2-chlorobenzyl chloride in 50 ml dried toluene. The crude product was distilled under reduced pressure to give, in three fractions, 2.07 g of c-5-(2-chlorobenzyloxy)-r-2-ethyl-c-4-propyl-1,3-dioxane; bp 120°–125°/0.01 mm. The nmr and the ir spectra were consistent with the assigned structure.

Analyses calc'd for $C_{16}H_{23}ClO_3$: C 64.31; H 7.76. Found: C 64.00; H 7.57.

EXAMPLE XIII r-2-Ethyl-c-4-methyl-t-5-(2-methylbenzyloxy)-1,3-dioxane

This compound was prepared in the manner of Example I, using 2.48 g of r-2-ethyl-t-5-hydroxy-c-4-methyl-1,3-dioxane, 2.60 g of 2-methylbenzyl chloride, and 0.45 g (0.90 g of a 50% dispersion in mineral oil) of sodium hydride in 70 ml of toluene. The crude reaction mixture was distilled to give 2.41 g of r-2-ethyl-c-4-methyl-t-5-(2-methylbenzyloxy)-1,3-dioxane; bp 93°–95°/0.011 mm, $n_D^{25}$=1.5284. The nmr and the ir spectra were consistent with the assigned structure.

Analyses calc'd for $C_{15}H_{22}O_3$: C 71.97; H 8.86. Found: C 72.60; H 8.90.

EXAMPLE XIV r-2-Ethyl-t-4, t-5, c-6-trimethyl-c-5-(2-methylbenzyloxy)-1,3-dioxane in mixture with what is believed to be 2-ethyl-4,5-dimethyl-4-[1-(2-methylbenzyloxy)ethyl]-1,3-dioxolane A stirred solution of 6.22 g of the mixture of r-2-ethyl-c-5-hydroxy-t-4, t-5, c-6-trimethyl-1,3-dioxane and what is believed to be 2-ethyl-4,5-dimethyl-4-(1-hydroxyethyl)-1,3-dioxolane and 2.42 g of sodium ethoxide (an ethanolic solution 15% in sodium ethoxide) in dry toluene was heated to a temperature which caused the ethanol to be removed azeotropically from the reaction mixture. Additional toluene was added to the reaction mixture as needed. When the temperature of the distillate reached 110°, 50 ml of the distillate was collected; and the reaction mixture cooled to ambient temperature. To the reaction mixture was added, in one portion, a solution of 5.02 g of 2-methylbenzyl chloride. The reaction mixture was heated under reflux for 20 hours, then poured into 50 ml cold water. The toluene layer was separated and the water layer washed with three portions of 50 ml each of toluene. The combined toluene layers were washed with three portions of 25 ml each of water, then dried with sodium sulfate. The mixture was filtered and the filtrate evaporated under reduced pressure to a residue.

The residue was distilled under reduced pressure using a short-path distilling system. One fraction of 3.09 g of distillate, bp 25°–42°/0.01 mm was obtained. Gas chromatographic analysis of this fraction indicated a mixture containing a large portion of starting o-methylbenzyl chloride. The distillation vessel residue from this distillation, weight 5.59 g, was distilled under reduced pressure to give in one fraction 4.58 g of clear liquid distillate, bp 118°–122°/0.07 mm. Gas chromatographic analysis of the distillate indicated it to be a mixture of 62% r-2-ethyl-t-4, t-5, c-6-trimethyl-c-5-(2-methylbenzyloxy)-1,3-dioxane and 23% of what is believed to be 2-ethyl-4,5-dimethyl-4-[1-(2-methylbenzyloxy)ethyl]-1,3-dioxolane. The nmr spectrum was consisted with the assigned structures.

EXAMPLE XV r-2-Ethyl-c-4, t-4, t-5-trimethyl-c-5-(2-methylbenzyloxy)-1,3-dioxane

This compound was prepared in the manner of Example I, using 5.78 g of r-2-ethyl-c-5-hydroxy-c-4, t-4, t-5-trimethyl-1,3-dioxane, 5.13 g of 2-methylbenzyl chloride, 0.88 g (1.75 g of a 50% dispersion with mineral oil) of sodium hydride in 100 ml of dry toluene.

The crude reaction product was subjected to column chromatography using 150 g of silica gel in a 3.6 cm (O.D.) glass column. Elution was accomplished with 100% high-boiling petroleum ether, 99:1 high-boiling petroleum ether/ethyl acetate, 95:5 high-boiling petroleum ether/ethyl acetate, and 100% ethyl acetate. Fractions 70–156 were combined to yield 4.19 g of residual oil, after evaporation of the solvents. The residual oil was distilled using a short-path distilling system to give, in two fractions, 1.06 g of r-2-ethyl-c-4-t-4,t-5-trimethyl-c-5-(2-methylbenzyloxy)-1,3-dioxane; bp 89.5°–93°/0.005 mm. The ir and the nmr spectra were consistent with the assigned structure.

Analyses calc'd for $C_{17}H_{26}O_3$: C 73.34; H 9.41. Found: C 73.38; H 9.56.

EXAMPLE XVI

(2α, 4aα, 8aβ)-2-Ethylhexahydro-4a-(2-methylbenzyloxy)-4H-1,3-benzodioxin

This compound was prepared in the manner of Example I, using 6.70 g of (2α, 4aα, 8aβ)-2-ethylhexahydro-4a-hydroxy-4H-1,3-benzodioxin, 0.95 g (1.90 g of a 50% mineral oil dispersion) of sodium hydride and 5.06 g of 2-methylbenzyl chloride, in 100 ml of dry dimethylformamide. The reaction mixture was heated at 75° for 21 hours. Gas chromatographic analysis of the reaction mixture indicated it to be 54.2% in the benzyloxy derivative. The reaction mixture was heated at 75° for an additional 16 hours. Gas chromatographic analysis of the reaction mixture indicated it to be still 54.2% in the benzyloxy derivative. The dimethylformamide was removed from the reaction mixture by distillation under reduced pressure using a Vigreux column, and keeping the head temperature below 50°. The yellow residue was slurried in 150 ml cold water and extracted with three portions of 150 ml each of diethyl ether. The combined extracts were washed with three portions of 150 ml each of cold water, then dried with sodium sulfate and filtered. The filtrate was evaporated under reduced pressure to a residue. The residue was distilled using a short-path distilling system to give 5.45 g of distillate that was 78.4% benzyloxy derivative by gas chromatographic analysis. The distillate was subjected to column chromatography using 105 g of silica gel in a 3 × 33 cm glass column. Elution was carried out using 100% high-boiling petroleum ether, and 99:1 high-boiling petroleum ether-ethyl acetate. Fractions 25-36 were combined to give 0.75 g of clear liquid. This liquid was distilled to give 0.66 g of clear liquid; bp 120°/0.025 mm.

Fractions 19-24 from the column chromatography were combined and distilled to give 0.82 g of clear liquid; bp 120°-125°/0.025 mm. Fractions 10-18 from the column chromatography were combined and distilled to give 1.90 g of clear liquid; bp 120°-125°/0.025 mm. The three distillates were combined to give 3.38 g of (2α, 4aα, 8aβ)-2-ethylhexahydro-4a-(2-methylbenzyloxy)-4H-1,3-benzodioxin, $n_D^{25}$=1.5206. The ir and the nmr spectra were consistent with the assigned structure.

Analyses calc'd for $C_{18}H_{26}O_3$: C74.44; H 9.03. Found: C 74.72; H 9.17.

EXAMPLE XVII (2α, 4aβ, 8aβ)-2-Ethylhexahydro-4a-(2-methylbenzyloxy)-4H-1,3-benzodioxin At ambient temperature, 4.86 g of (2α, 4aβ, 8aβ)-2-ethylhexahydro-4a-hydroxy-4H-1,3-benzodioxin was reacted with 1.95 g (2.05 g of a 96% pure sample) of sodium ethoxide in ethanol. The reaction mixture was heated to a temperature where the periodic addition of toluene caused the ethanol to be removed azeotropically from the reaction mixture. When the temperature of the distillate reached 110°, the reaction mixture was cooled to ambient temperature and 3.67 g of 2-methylbenzyl chloride was added during one minute. Upon complete addition the reaction mixture was heated under reflux during 45 hours, then poured into 150 ml of an aqueous solution saturated with sodium chloride. The toluene layer was separated and washed with two portions of 150 ml each of an aqueous solution saturated with sodium chloride, then dried with sodium sulfate. The mixture was filtered and the filtrate evaporated under reduced pressure to a residual oil. The residual oil was distilled in three fractions to give 6.73 g of distillate; bp 54°-130°/0.25 mm. The third fraction, 2.17 g; bp 80°-130°/0.25 mm, was placed on a column of 30 g of silica gel (2.1 × 28 cm) and eluted with 100% high-boiling petroleum ether and 99:1 high-boiling petroleum ether-ethyl acetate. Of the 28 fractions taken, fractions 1-7 were discarded, fractions 8-11 and 16-20 were combined to give 1.34 g of liquid, and fractions 12-15 were combined to yield 0.23 g of liquid. The liquid obtained from the combination of fractions 8-11 and 16-20 was again placed on a column of silica gel, as previously described, and eluted with solvent mixtures as previously described. Of the 25 fractions taken, fractions 1-11 were discarded, fractions 12-19 were combined to give 0.78 g of product, and fractions 20-23 were combined to give 0.44 g of product. The liquids obtained from these combinations were separately distilled using a micro distillation apparatus to give a total of 1.07 g of 92% pure (2α, 4aβ, 8aβ)-2-ethylhexahydro-4a-(2-methylbenzyloxy)-4H-1,3-benzodioxin. The nmr spectrum was consistent with the assigned structure.

Analyses calc'd for $C_{18}H_{26}O_3$: C 74.44; H 9.03. Found: 74.16; H 8.97.

The herbicidal activities of the compounds of this invention were demonstrated as follows: Rows of seeds of lima beans (Phaseolus lunatus), corn (Zea mays), wild oats (Avena fatua), lettuce (Lactuca sativa), mustard (Brassica juncea) and crabgrass (Digitaria sanguinalis) were planted in shallow flat-bed trays (20 cm × 15 cm × 8 cm) containing approximately 5 cm of sandy loam soil, and a thin layer of soil (approximately 1 cm) was applied to the surface to cover the seeds. Pots containing viable tubers of purple nutsedge (Cyperus rotundus) planted at a depth of 2.5 cm were used.

For preemergence tests, an aqueous acetone solution of the test compound (using sufficient acetone to obtain solution) was sprayed on the soil covering the seeds in the trays (or the tubers in the pots) at a rate equivalent to 8.96 kilograms/hectare or submultiples thereof (4.48, 2.24, 1.12, 0.56, 0.28 kg/ha), using a total volume equivalent to 760 liters/hectare. The trays and pots were maintained under intermittent high-intensity light conditions in the greenhouse for 10 to 14 days, after which the herbicidal efficacy of the compound was assessed. Individual plant species were examined in comparison with untreated plants. Tables 1, 2, 3, and 4 list results collected in preemergence tests with compounds of the present invention, shown together with results obtained in parallel tests of compounds within the scope of U.S. Pat. No. 3,753,678 (which bear only hydrogen on the carbons in the 4-position and the 6-position of the 1,3-dioxane).

In Table 1 it is seen that compounds of Examples I, II, III, and IV are herbicidally active against grassy species such as corn and crabgrass at rates of application of 0.56 kg/ha or below, while the standard for comparison, a prior art 1,3-dioxane with only hydrogen in the 4- and 6-positions is clearly less active. The compounds of Examples I, II, and III are also approximately twice as effective against purple nutsedge at rates of 2.24 kg/hectare as the prior art comparison compound. The compound of Example XV is seen to be altogether inactive at 4.48 Kg/ha or below, and shows only a trace of activity against corn and crabgrass at 8.96 kg/ha. This compound differs from the prior art comparison compound in having two methyl groups in the 4-position of the dioxane ring, and is essentially without herbicidal activity. The compound of Example XIII is seen to be totally inactive at 8.96 kg/ha. This compound differs from the compound of Example II only in the stereochemical relationship between the 2-ethyl substituent and the 5-(2-methylbenzyloxy) substituent. In the active compound of Example II there is a cis relationship between these substituents, and in the inactive compound of Example XIII, there is a trans relationship between these substituents.

In Table 2 the bicyclic compound of Example XVI is seen to have herbicial activity of the same order as that of the prior art reference compound, and the bicyclic compound of Example XVII is seen to be herbicidally inactive at 4.48 kg/ha or below. These compounds differ in the orientation of the cyclohexyl ring fused to the dioxane ring at the 4- and 5-carbons. The compound of Example XVI is fused in a trans position relative to the 2-substituent in the dioxane ring, leaving the 5-benzyloxy substituent cis relative to the 2-substituent. In the compound of Example XVII, the cyclohexyl ring is fused in a cis position relative to the 2-substituent in the dioxane, displacing the 5-benzyloxy substituent from cis relationship with the 2-substituent and completely destroying herbicidal activity.

Other varieties of plant species were used for further preemergence evaluations. These included coffeeweed (Sesbania spp.), sugarbeet (*Beta vulgaris*), soybeans (*Glycine max*), cotton (*Gossypium hirsutum*), sorghum (*Sorghum vulgare*), sicklepod (*Cassia obtusifolia*), barley (*Hordeum vulgare*), barnyardgrass (*Echinochloa crusgalli*), peanut (*Arachis hypogaea*), safflower (*Carthamus tinctorious*), tomato (*Lycopersicon esculentum*, rice (*Oryza sativa*), wheat (*Triticum aestivum*, morningglory (*Impomoea purpurea*), rape (*Brassica campestris*), prickly sida (*Sida spinosa* L.), giant foxtail (*Setaria faberii*), oats (*Avena sativa*), downy brome (*Bromus tectorum*), and sesbania (*Sesbania exaltata*).

An extended evaluation of compounds of the invention compared the compound of Example I with Comparison Standard A, the compound of Example II with Comparison Standard B, and the compound of Example III with Comparison Standard C. The comparison Standards are within the scope of U.S. Pat. No. 3,753,678 and A, B, and C each differs from the compound with which it is being compared only in having no 4-substituent. Inspection of Table 3, in which the results of these comparisons are recorded, shows the 4-substituted dioxanes of the present invention to be more active than their prior art counterparts without 4-substitution. In addition the prior art dioxane (Comparison Standard D) with a 5-methyl substituent instead of the 4-methyl substituent of the compounds of the present invention was again found less herbicidally active against corn, wild oats, crabgrass, barnyardgrass, giant foxtail, oats, barley, and rice than the compounds of the present invention. The compounds of the present invention were less toxic to wheat than the prior art dioxane, and were non-toxic to lettuce, tomato, peanut, and essentially non-toxic to soybeans, cotton, and sugarbeet, at rates of 4.48 kg/ha or less.

The results recorded in Table 4 show the compounds of Example XIV (a mixture of 62% dioxane and 23% dioxolane) to be slightly less active than the prior art dioxane. The dioxane of Example XIV contains a methyl group in the 5-position, as does the prior art dioxane, and a methyl group in the 4-position, as does the preferred compound of the present invention, and a methyl group in the 6-position.

For postemergence tests, the trays in which seeds had been planted were maintained in the greenhouse until the first trifoliate leaves of the bean plants were unfolding. The test plants were then sprayed with an aqueous acetone solution of test compound as for preemergence tests. The plants were returned to the greenhouse and held under intermittent high-intensity light conditions for 10 to 14 days, after which the herbicidal efficacy of the compound was assessed. Table 5 lists results collected in post-emergence tests with compounds of the present invention.

For herbicidal application, the active 1,3-dioxanes of this invention may be utilized in diverse formulations including the agricultural adjuvants and agricultural carriers to produce the herbicidal compositions contemplated herein. The herbicidal compositions contain between about 0.01% and 95% active 1,3-dioxane together with between about 4% and 98.5% agriculturally acceptable carrier and between about 1% and 15% surface active agent by weight. As is well-known in the art, the formulation and mode of application of a toxicant may affect the activity of the material in a given application. Thus, a compound of this invention may be formulated as an emulsifiable concentrate, as a granule of relatively large particle size, as a wettable powder, as a solution, or as any of several other known types of formulations, depending on the desired mode of applications.

emulsifiable concentrates are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other nonvolatile organic solvents. For example, a useful emulsifiable concentrate formulation, designated "4EC" because it contains four pounds of active ingredient per gallon of concentrate (0.479 kg/liter), contains 53.01 parts of r-2-ethyl-c-4-methyl-c-5-(2-methylbenzyloxy)-1,3-dioxane, 6.0 parts of a blend of alkylnaphthalenesulfonate and polyoxyethylene ethers as emulsifiers, 1.0 part of epoxidized soybean oil as stabilizer, and as solvent 39.99 parts of petroleum distillate having a high flash-point.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be watersoluble such as a prilled fertilizer, or insoluble such as sand, marble chips or coarse talc. Particularly useful is a granule wherein a wettable powder is applied as a surface coating to a sand or other insoluble particle such that the wettable powder may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5% or as much as 95% of active ingredient.

Wettable powders, also useful formulations for both pre- and postemergency herbicides, are in the form of finely divided particles which disperse readily in water or other dispersants. The wettable powder is ultimately applied to the soil or to the undesired plant growth either as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion.

Typical wetting, dispersing or emulsifying agents used in agricultural formulations include, for example, the alkyl and alkylaryl sulfonates and sulfates and their sodium salts; polyethylene oxides; sulfonated oils; fatty acid esters of polyhydric alcohols; and other types of surface-active agents, many of which are available in commerce. The surface-active agent, when used, normally comprises from 1 to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant-growth regulators, fertilizers, and other agricultural chemicals. In applying the active compounds of this invention, whether formulated alone or with other agricultural chemicals, an effective amount and concentration of 1,3-dioxane are of course employed. The amount constituting an effective amount is variable, but generally, a uniform application of between 0.1 and 9 kilograms per hectare is effective, for example, 0.28 to 4.48 kilograms per hectare.

It is apparent that various modifications may be made in the formulation and application of the novel compounds of this invention, without departing from the inventive concept herein, as defined in the following claims:

Table 1

Preemergence Herbicidal Activity of 4-Substituted-1,3-Dioxanes

| Compound of Example | plant Species | Percent Kill at indicated rates of application in kilograms/hectare | | | | | |
|---|---|---|---|---|---|---|---|
| | | 0.28 | 0.56 | 1.12 | 2.24 | 4.48 | 8.96 |
| I | Lima Bean | — | 0 | 0 | 10 | 60* | 80* |
| | Corn | — | 100 | 100 | 100 | 100 | 100 |
| | Wild Oats | — | 100 | 95* | 100 | 100 | 100 |
| | Lettuce | — | 0 | 0 | 0 | 0 | 0 |
| | Mustard | — | 0 | 0 | 0 | 0* | 0* |
| | Crabgrass | — | 100 | 100 | 100 | 100 | 100 |
| | Nutsedge | — | 0 | 0 | 0 | 75* | 75* |
| II | Lima Bean | — | 0 | 0 | 0 | 40* | 90* |
| | Corn | — | 100 | 100 | 100 | 100 | 100 |
| | Wild Oats | — | 40 | 95* | 95* | 100 | 100 |
| | Lettuce | — | 0 | 0 | 0 | 0 | 0 |
| | Mustard | — | 0 | 0 | 0 | 10* | 0 |
| | Crabgrass | — | 100 | 100 | 100 | 100 | 100 |
| | Nutsedge | — | 75 | 25 | 50 | 75* | 100 |
| III | Lima Bean | — | 0 | 0 | 0 | 10 | 90* |
| | Corn | — | 100 | 100 | 100 | 100 | 100 |
| | Wild Oats | — | 10 | 90* | 95* | 100 | 100 |
| | Lettuce | — | 0 | 0 | 0 | 0 | 0 |
| | Mustard | — | 0 | 0 | 0 | 0 | 10* |
| | Crabgrass | — | 100 | 100 | 100 | 100 | 100 |
| | Nutsedge | — | 0 | 0 | 40 | 80* | 100 |
| IV | Lima Beans | 0 | 0 | 0 | 0 | 0* | 0* |
| | Corn | 70* | 100 | 100 | 100 | 100 | 100 |
| | Wild Oats | 20 | 40 | 80* | 100 | 100 | 100 |
| | Lettuce | 0 | — | 0 | 0 | 0 | 0 |
| | Mustard | 0 | 0 | 0 | 0 | 60* | 100 |
| | Crabgrass | 100 | 100 | 100 | 100 | 100 | 100 |
| | Nutsedge | — | — | — | — | — | — |
| XIII | Lima Beans | — | — | — | — | — | 0 |
| | Corn | — | — | — | — | — | 0 |
| | Wild Oats | — | — | — | — | — | 0 |
| | Lettuce | — | — | — | — | — | 0 |
| | Mustard | — | — | — | — | — | 0 |
| | Crabgrass | — | — | — | — | — | 0 |
| XV | Lima Beans | — | 0 | 0 | 0 | 0 | 0 |
| | Corn | — | 0 | 0 | 0 | 0 | 30 |
| | Wild Oats | — | 0 | 0 | 0 | 0 | 0 |
| | Lettuce | — | 0 | 0 | 0 | 0 | 0 |
| | Mustard | — | 0 | 0 | 0 | 0 | 0 |
| | Crabgrass | — | 0 | 0 | 0 | 0 | 0 |
| | Nutsedge | — | 0 | 0 | 0 | 0 | 0 |
| Standard** for Comparison | Lima Beans | — | 0 | 0 | 0 | — | — |
| | Corn | — | 0 | 70* | 70* | — | — |
| | Wild Oats | — | 0 | 0 | 40 | — | — |
| | Lettuce | — | 0 | 0 | 0 | — | — |
| | Mustard | — | 0 | 0 | 0 | — | — |
| | Crabgrass | — | 0 | 100 | — | — | — |

Table 1-continued

Preemergence Herbicidal Activity of 4-Substituted-1,3-Dioxanes

| Compound of Example | plant Species | Percent Kill at indicated rates of application in kilograms/hectare | | | | | |
|---|---|---|---|---|---|---|---|
| | | 0.28 | 0.56 | 1.12 | 2.24 | 4.48 | 8.96 |
| | Nutsedge | — | 0 | 0 | 25 | — | — |

*Plants not dead were severely damaged and not expected to live.
**r-2-Ethyl-5-methyl-c-5-(2-methylbenzyloxy)-1,3-dioxane.

Table 2

Preemergence Herbicidal Activity of 4-Substituted-1,3-Dioxanes

| Compound of Example | Plant Species | Percent kill at indicated rates of application in kilograms/hectare | | | | | |
|---|---|---|---|---|---|---|---|
| | | 0.28 | 0.56 | 1.12 | 2.24 | 4.48 | 8.96 |
| XVI | Lima Beans | 0 | 0 | 0 | 0 | 0 | 0 |
| | Corn | 0 | 0 | 0 | 30 | 100 | 100 |
| | Wild Oats | 0 | 70 | 70 | 80* | 100 | 80 |
| | Lettuce | 0 | 0 | 0 | 0 | 0 | 0 |
| | Mustard | 0 | 0 | 0 | 0 | 0 | 0 |
| | Crabgrass | 30 | 50* | 70* | 100 | 100 | 100 |
| XVII | Lima Beans | 0 | 0 | 0 | 0 | 0 | — |
| | Corn | 0 | 0 | 0 | 0 | 0 | — |
| | Wild Oats | 0 | 0 | 0 | 0 | 0 | — |
| | Lettuce | 0 | 0 | 0 | 0 | 0 | — |
| | Mustard | 0 | 0 | 0 | 0 | 0 | — |
| | Crabgrass | 0 | 0 | 0 | 0 | 0 | — |
| Standard** for Comparison | Lima Beans | 0 | 0 | 0 | 0 | — | — |
| | Corn | 0 | 70 | 100 | 100 | — | — |
| | Wild Oats | 50 | 50 | 80* | 100 | — | — |
| | Lettuce | 0 | 0 | 0 | 0 | — | — |
| | Mustard | 0 | 0 | 0 | 0 | — | — |
| | Crabgrass | 0 | 30 | 50* | 50* | — | — |

*Plants not dead were severely damaged and not expected to live.
**r-2-Ethyl-5-methyl-c-5-(2-methylbenzyloxy)-1,3-dioxane.

Table 2A

Preemergence Herbicidal Activity of 4-Substituted-1,3-Dioxanes

| Compound of Example | Plant Species | Percent kill at indicated rates of application in kilograms/hectare | | | | | |
|---|---|---|---|---|---|---|---|
| | | 0.28 | 0.56 | 1.12 | 2.24 | 4.48 | 8.96 |
| V | Lima Beans | 0 | 0 | 0 | 0 | 0 | 0 |
| | Corn | 0 | 100 | 100 | 100 | 100 | 100 |
| | Wild Oats | 0 | 0 | 0 | 0 | 0 | 100 |
| | Lettuce | 0 | 0 | 0 | 0 | 0 | 0 |
| | Mustard | 0 | 0 | 0 | 0 | 0 | 0 |
| | Crabgrass | 0 | 95* | 100 | 100 | 100 | 100 |
| | Nutsedge | — | 0 | 0 | 0 | 30 | 0 |
| VI | Lima Beans | 0 | 0 | 0 | 0 | 0 | 0 |
| | Corn | 60 | 100 | 100 | 100 | 100 | 100 |
| | Wild Oats | 0 | 0 | 0 | 20 | 80 | 100 |
| | Lettuce | 0 | 0 | 0 | 0 | 0 | 0 |
| | Mustard | 0 | 0 | 0 | 0 | 0 | 0 |
| | Crabgrass | 90* | 90* | 100 | 100 | 100 | 100 |
| | Nutsedge | — | 0 | 0 | 75 | 75 | 100 |
| VII | Lima Beans | 0 | 0 | 0 | 0 | 0 | 0 |
| | Corn | 30 | 60 | 100 | 100 | 100 | 100 |
| | Wild Oats | 0 | 0 | 0 | 0 | 80* | 80* |
| | Lettuce | 0 | 0 | 0 | 0 | 0 | 0 |
| | Mustard | 0 | 0 | 0 | 0 | 0 | 0 |
| | Crabgrass | 80 | 100 | 100 | 100 | 100 | 0 |
| | Nutsedge | — | 0 | 0 | 75 | 75* | 100 |
| VIII | Lima Beans | 0 | 0 | 0 | 0 | 0 | 0 |
| | Corn | 60 | 100 | 100 | 100 | 100 | 100 |
| | Wild Oats | 0 | 0 | 30 | 50 | 100 | 0 |
| | Lettuce | — | 0 | 0 | 0 | 0 | 0 |
| | Mustard | 0 | 0 | 0 | 0 | 0 | 0 |
| | Crabgrass | 100 | 100 | 95* | 100 | 100 | 100 |
| | Nutsedge | — | 0 | 0 | 20 | 50 | 75* |
| Standard** for Comparison | Lima Beans | 0 | 0 | 0 | 0 | — | — |
| | Corn | 0 | 30* | 100 | 100 | — | — |
| | Wild Oats | 0 | 0 | 0 | 0 | — | — |
| | Lettuce | 0 | 0 | 0 | 0 | — | — |
| | Mustard | 0 | 0 | 0 | 0 | — | — |
| | Crabgrass | 80* | 90* | 80* | 90* | — | — |
| | Nutsedge | — | 0 | 50 | 100 | — | — |

*Plants not dead were severely damaged and not expected to live.
**r-2-Ethyl-5-methyl-c-5-(2-methylbenzyloxy)-1,3-dioxane.

Table 3

Extended Evaluation of Preemergence Herbicidal Activity of 4-Substituted 1,3-Dioxanes

| Compound of Example | Plant Species | % Kill at Indicated Rate of Application in kilograms/hectare | | | | |
|---|---|---|---|---|---|---|
| | | 0.28 | 0.56 | 1.12 | 2.24 | 4.48 |
| I | Lima Bean | 0 | 0 | 0 | 0 | 0* |
| | Corn | 0 | 100 | 100 | 100 | 100 |
| | Wild Oats | 0 | 0 | 20 | 50 | 100 |
| | Lettuce | 0 | 0 | 0 | 0 | 0 |
| | Mustard | 0 | 0 | 0 | 0 | 0* |
| | Crabgrass | 90* | 100 | 100 | 100 | 100 |
| | Soybean | 0 | 0 | 0 | 0 | 0 |
| | Cotton | 0 | 0 | 0 | 0 | 0 |
| | Morningglory | 0 | 0 | 0 | 0 | 0 |
| | Sesbania | 0 | 0 | 0 | 0 | 0* |
| | Barnyardgrass | 20 | 70* | 70* | 100 | 100 |
| | Giant Foxtail | 30 | 70* | 100 | 100 | 100 |
| | Downy Brome | 0 | 0 | 20 | 40 | 80* |
| | Sicklepod | 0 | 0 | 0 | 0 | 0 |
| | Prickly Sida | 0 | 0 | 0 | 0 | 0 |
| | Wheat | 0 | 0 | 0 | 0 | 20 |
| | Sorghum | 0 | 20 | 70 | 100 | 100 |
| | Oats | 10 | 50 | 80* | 80* | 100 |
| | Barley | 60* | 100 | 100 | 100 | 100 |
| | Sugarbeet | 0 | 0 | 0 | 0 | 0* |
| | Tomato | 0 | 0 | 0 | 0 | 0 |
| | Rice | 80* | 100 | 100 | 100 | 100 |
| | Safflower | 0 | 0 | 0 | 0* | 50* |
| | Peanut | 0 | 0 | 0 | 0 | 0 |
| | Rape | 0 | 0 | 0 | 0 | 0 |
| Comparison Standard A | Lima Bean | 0 | 0 | 0 | 0 | 0 |
| | Corn | 0 | 0 | 30 | 100 | 100 |
| | Wild Oats | 0 | 0 | 20 | 40 | 60 |
| | Lettuce | 0 | 0 | 0 | 0 | 0 |
| | Mustard | 0 | 0 | 0 | 0 | 0 |
| | Crabgrass | 0 | 20 | 50 | 100 | 100 |
| | Soybean | 0 | 0 | 0 | 0 | 0 |
| | Cotton | 0 | 0 | 0 | 0 | 0 |
| | Morningglory | 0 | 0 | 0 | 0 | 0 |
| | Sesbania | 0 | 0 | 0 | 0 | 0 |
| | Barnyardgrass | 0 | 10 | 30 | 100 | 100 |
| | Giant Foxtail | 0 | 30 | 50 | 70 | 100 |
| | Downy Brome | 0 | 0 | 0 | 40 | 100 |
| | Sicklepod | 0 | 0 | 0 | 0 | 0 |
| | Prickly Sida | 0 | 0 | 0 | 0 | 0 |
| | Wheat | 0 | 0 | 0 | 0 | 0 |
| | Sorghum | 0 | 0 | 0 | 100 | 100 |
| | Oats | 0 | 0 | 20 | 70* | 100 |
| | Barley | 0 | 20 | 80* | 100 | 100 |
| | Sugarbeet | 0 | 0 | 0 | 0 | 0 |
| | Tomato | 0 | 0 | 0 | 0 | 0 |
| | Rice | 0 | 0 | 50 | 100 | 100 |
| | Safflower | 0 | 0 | 0 | 0 | 0 |
| | Peanut | 0 | 0 | 0 | 0 | 0 |
| | Rape | 0 | 0 | 0 | 0 | 0 |
| II | Lima Bean | 0 | 0 | 0 | 0 | 0* |
| | Corn | 30 | 100 | 100 | 100 | 100 |
| | Wild Oats | 0 | 40 | 70* | 100 | 100 |
| | Lettuce | 0 | 0 | 0 | 0 | 0 |
| | Mustard | 0 | 0 | 0 | 0 | 50* |
| | Crabgrass | 70* | 100 | 100 | 100 | 100 |
| | Soybeans | 0 | 0 | 0 | 0 | 0* |
| | Cotton | 0 | 0 | 0 | 0 | 0* |
| | Morningglory | 0 | 0 | 0 | 0 | 0 |
| | Sesbania | 0 | 0 | 0 | 0 | 0* |
| | Barnyardgrass | 30 | 50 | 100 | 100 | 100 |
| | Giant Foxtail | 20 | 30 | 50* | 100 | 100 |
| | Downy Brome | 0 | 0 | 0 | 50 | 70* |
| | Sicklepod | 0 | 0 | 0 | 0 | 0* |
| | Prickly Sida | 0 | 0 | 0 | 0 | 0* |
| | Wheat | 0 | 0 | 0 | 0 | 30 |
| | Sorghum | 0 | 40 | 70* | 90* | 100 |
| | Oats | 50 | 70 | 80* | 100 | 100 |
| | Barley | 50* | 100 | 100 | 100 | 100 |
| | Sugarbeet | 0 | 0 | 0 | 0 | 0 |
| | Tomato | 0 | 0 | 0 | 0 | 0 |
| | Rice | 80* | 100 | 100 | 100 | 100 |
| | Safflower | 0 | 0 | 0 | 0 | 40 |
| | Peanut | 0 | 0 | 0 | 0 | 0 |
| | Rape | 0 | 0 | 0 | 0 | 0* |
| Comparison Standard B | Lima Bean | 0 | 0 | 0 | 0 | 0 |
| | Corn | 0 | 0 | 70 | 30 | 100 |
| | Wild Oats | 0 | 0 | 0 | 0 | 40 |
| | Lettuce | 0 | 0 | 0 | 0 | 0 |
| | Mustard | 0 | 0 | 0 | 0 | 0 |
| | Crabgrass | 50 | 50 | 70 | 70* | 100 |
| | Soybeans | 0 | 0 | 0 | 0 | 0 |
| | Cotton | 0 | 0 | 0 | 0 | 0 |
| | Morningglory | 0 | 0 | 0 | 0 | 0 |
| | Sesbania | 0 | 0 | 0 | 0 | 0 |
| | Barnyardgrass | 0 | 0 | 30 | 70 | 70* |
| | Giant Foxtail | 0 | 50 | 30 | 50 | 60* |
| | Downy Brome | 0 | 0 | 0 | 30 | 70 |
| | Sicklepod | 0 | 0 | 0 | 0 | 0 |
| | Prickly Sida | 0 | 0 | 0 | 0 | 0 |
| | Wheat | 0 | 0 | 0 | 0 | 20 |
| | Sorghum | 0 | 0 | 0 | 0 | 30 |
| | Oats | 0 | 0 | 0 | 40 | 70 |
| | Barley | 0 | 30 | 50 | 80* | 100 |
| | Sugarbeet | 0 | 0 | 0 | 0 | 0 |
| | Tomato | 0 | 0 | 0 | 0 | 0 |
| | Rice | 0 | 0 | 30 | 50 | 100 |
| | Safflower | 0 | 0 | 0 | 0 | 0 |
| | Peanut | 0 | 0 | 0 | 0 | 0 |
| | Rape | 0 | 0 | 0 | 0 | 0 |
| III | Lima Bean | 0 | 0 | 0 | 0 | 0 |
| | Corn | 0 | 100 | 100 | 100 | 100 |
| | Wild Oats | 10 | 30 | 30 | 70 | 100 |
| | Lettuce | 0 | 0 | 0 | 0 | 0 |
| | Mustard | 0 | 0 | 0 | 0 | 0* |
| | Crabgrass | 100 | 100 | 100 | 100 | 100 |
| | Soybeans | 0 | 0 | 0 | 0 | 0* |
| | Cotton | 0 | 0 | 0 | 0 | 0 |
| | Morningglory | 0 | 0 | 0 | 0 | 0 |
| | Sesbania | 0 | 0 | 0 | 0 | 0 |
| | Barnyardgrass | 20 | 90* | 100 | 100 | 100 |
| | Giant Foxtail | 50 | 90* | 100 | 100 | 100 |
| | Downy Brome | 0 | 0 | 20 | 30 | 80* |
| | Sicklepod | 0 | 0 | 0 | 0 | 0 |
| | Prickly Sida | 0 | 0 | 0 | 0 | 0* |
| | Wheat | 0 | 0 | 0 | 0 | 20 |
| | Sorghum | 0 | 0 | 0 | 0 | 20 |
| | Oats | 30 | 50 | 70* | 80* | 100 |
| | Barley | 30 | 50 | 100 | 100 | 100 |
| | Sugarbeet | 0 | 0 | 0 | 0 | 0 |
| | Tomato | 0 | 0 | 0 | 0 | 0 |
| | Rice | 50 | 100 | 100 | 100 | 100 |
| | Safflower | 0 | 0 | 0 | 0 | 50 |
| | Peanut | 0 | 0 | 0 | 0 | 0 |
| | Rape | 0 | 0 | 0 | 0 | 0* |
| Comparison Standard C | Lima Bean | 0 | 0 | 0 | 0 | 0 |
| | Corn | 0 | 0 | 0 | 30 | 100 |
| | Wild Oats | 0 | 0 | 0 | 0 | 20 |
| | Lettuce | 0 | 0 | 0 | 0 | 0 |
| | Mustard | 0 | 0 | 0 | 0 | 0 |
| | Crabgrass | 50 | 50 | 80* | 100 | 100 |
| | Soybeans | 0 | 0 | 0 | 0 | 0 |
| | Cotton | 0 | 0 | 0 | 0 | 0 |
| | Morningglory | 0 | 0 | 0 | 0 | 0 |
| | Sesbania | 0 | 0 | 0 | 0 | 0 |
| | Barnyardgrass | 0 | 0 | 20 | 70 | 90* |
| | Giant Foxtail | 0 | 70 | 100 | 70 | 100 |
| | Downy Brome | 0 | 0 | 0 | 0 | 20 |
| | Sicklepod | 0 | 0 | 0 | 0 | 0 |
| | Prickly Sida | 0 | 0 | 0 | 0 | 0 |
| | Wheat | 0 | 0 | 0 | 0 | 0 |
| | Sorghum | 0 | 0 | 0 | 20 | 60 |
| | Oats | 0 | 0 | 0 | 30 | 60 |
| | Barley | 0 | 0 | 0 | 50 | 100 |
| | Sugarbeet | 0 | 0 | 0 | 0 | 0 |
| | Tomato | 0 | 0 | 0 | 0 | 0 |
| | Rice | 0 | 0 | 50 | 50 | 80 |
| | Safflower | 0 | 0 | 0 | 0 | 0 |
| | Peanut | 0 | 0 | 0 | 0 | 0 |
| | Rape | 0 | 0 | 0 | 0 | 0 |
| Comparison Standard D | Lima Bean | 0 | 0 | 0 | 0 | 0 |
| | Corn | 0 | 0 | 0 | 30 | 100 |
| | Wild Oats | 0 | 0 | 0 | 20 | 60 |
| | Lettuce | 0 | 0 | 0 | 0 | 0 |
| | Mustard | 0 | 0 | 0 | 0 | 0* |
| | Crabgrass | 0 | 0 | 60 | 100 | 100 |
| | Soybeans | 0 | 0 | 0 | 0 | 0 |
| | Cotton | 0 | 0 | 0 | 0 | 0 |
| | Morningglory | 0 | 0 | 0 | 0 | 0 |
| | Sesbania | 0 | 0 | 0 | 0 | 0 |
| | Barnyardgrass | 0 | 30 | 40 | 70* | 100 |
| | Giant Foxtail | 0 | 0 | 0 | 60 | 70 |
| | Downy Brome | 0 | 0 | 0 | 20 | 80 |
| | Sicklepod | 0 | 0 | 0 | 0 | 0 |
| | Prickly Sida | 0 | 0 | 0 | 0 | 0 |
| | Wheat | 0 | 0 | 0 | 20 | 60 |
| | Sorghum | 0 | 0 | 0 | 20 | 70* |
| | Oats | 0 | 0 | 20 | 70 | 100 |
| | Barley | 0 | 50* | 70* | 100 | 100 |
| | Sugarbeet | 0 | 0 | 0 | 0 | — |
| | Tomato | 0 | 0 | 0 | 0 | 0 |
| | Rice | 0 | 30 | 50 | 100 | 100 |
| | Safflower | 0 | 0 | 0 | 0 | 0* |
| | Peanut | 0 | 0 | 0 | 0 | 0 |

Table 3-continued

Extended Evaluation of Preemergence Herbicidal Activity of 4-Substituted 1,3-Dioxanes

| Compound of Example | Plant Species | % Kill at Indicated Rate of Application in kilograms/hectare | | | | |
|---|---|---|---|---|---|---|
| | | 0.28 | 0.56 | 1.12 | 2.24 | 4.48 |
| | Rape | 0 | 0 | 0 | 0 | 0* |

Comparison Standards:
A cis-2-Ethyl-5-(2-fluorobenzyloxy)-1,3-dioxane.
B cis-2-Ethyl-5-(2-methylbenzyloxy)-1,3-dioxane.
C cis-2-Ethyl-5-(2-chlorobenzyloxy)-1,3-dioxane.
D r-2-Ethyl-5-methyl-c-5-(2-methylbenzyloxy)-1,3-dioxane.
*Plants not dead were severely damaged and not expected to live.

Table 4

Extended Evaluation of the Preemergence Herbicidal Activity of 4-Substituted-1,3-Dioxanes

| Compound of Example | Plant Species | % Kill at Indicated Rate of Application in kilograms/hectare | | | | |
|---|---|---|---|---|---|---|
| | | 0.56 | 1.12 | 2.24 | 4.48 | 8.96 |
| XIV | Lima Bean | 0 | 0 | 0 | 0 | — |
| | Corn | 0 | 70 | 100 | 100 | 100 |
| | Giant Foxtail | 0 | 30 | 70 | 70* | 80* |
| | Coffeeweed | 0 | 0 | 0 | 0 | 0 |
| | Sicklepod | 0 | 0 | 0 | 0 | 0 |
| | Soybeans | 0 | 0 | 0 | 0 | 0 |
| | Wild Oats | 30 | 70 | 70 | 70 | 70 |
| | Crabgrass | 70* | 100 | 100 | 100 | 100 |
| | Barnyardgrass | 50 | 70 | 100 | 100 | 100 |
| | Cotton | 0 | 0 | 0 | 0 | 0 |
| Standard** for Comparison | Lima Bean | 0 | 0 | 0 | 0 | 0 |
| | Corn | 30 | 100 | 100 | 100 | 100 |
| | Giant Foxtail | 30 | 70 | 100 | 100 | 100 |
| | Coffeeweed | 0 | 0 | 0 | 0 | 0 |
| | Sicklepod | 0 | 0 | 0 | 0 | 0 |
| | Soybeans | 0 | 0 | 0 | 0 | 0 |
| | Wild Oats | 50 | 50 | 70 | 60 | 80* |
| | Crabgrass | 70 | 100 | 100 | 100 | 100 |
| | Barnyardgrass | 70 | 100 | 100 | 100 | 100 |
| | Cotton | 0 | 0 | 0 | 0 | 0 |

*Plants not dead were severely damaged and not expected to live.
**r-2-Ethyl-5-methyl-c-5-(2-methylbenzyloxy)-1,3-dioxane.

Table 5

Post-emergence Herbicidal Activity of 4-Substituted-1,3-Dioxanes (% kill at 8.96 kg/ha)

| Compound of Example | Lima Bean | Corn | Wild Oats | Lettuce | Mustard | Crabgrass |
|---|---|---|---|---|---|---|
| I | 0 | 30* | 0 | 20 | 0 | 100 |
| II | 0 | 70* | 0 | 20 | 10 | 90* |
| III | 0 | 0* | 0 | 100 | 40* | 100 |
| IV | 0 | 70* | 40 | 0 | 0 | 90* |
| V | 0 | 0 | 50 | — | 0 | 100 |
| VI | 0 | 0 | 30 | — | 0 | 60 |
| VII | 0 | 0 | 20 | 0 | 0 | 0 |
| VIII | 0 | 0 | 20 | 0 | 0 | 0 |
| XIII | 0 | 0 | 0 | 0 | 0 | 0 |
| XV | 0 | 0 | 0 | 0 | 0 | 0 |

*Plants not dead were severely damaged and not expected to live.

I claim

1. A compound of the formula:

$$R^2\text{—}\underset{H}{\overset{O\text{—}CH_2}{\diagdown}}\underset{O\text{—}CH}{\diagup}\underset{R^4}{\overset{OCH_2\text{—}}{\diagdown}}\text{—}\langle\text{phenyl}\rangle\text{—}X_n$$

wherein
R² is alkyl of 1 to 4 carbon atoms;
R⁴ is alkyl of 1 to 4 carbon atoms;
R⁵ is hydrogen or alkyl of 1 to 4 carbon atoms;
X is chloro, fluoro, or methyl; and
n is 0, 1 or 2; is which the benzyloxy group bears a cis-relationship to R².

2. A compound of claim 1 in which R² is methyl, ethyl, propyl, isopropyl, or tert-butyl; R⁴ is methyl, ethyl, propyl, isopropyl, or tert-butyl; n is 0 or 1; X is chloro or methyl in the 2-position of the phenyl ring, and R⁴ bears a cis-relationship to R².

3. The compound of claim 1 which is c-5-benzyloxy-r-2-ethyl-c-4-methyl-1,3-dioxane.

4. The compound of claim 1 which is r-2-ethyl-c-5-(2-fluorbenzyloxy)-c-4-methyl-1,3-dioxane.

5. The compound of claim 1 which is r-2-ethyl-c-5-(2-methylbenzyloxy)-c-4-methyl-1,3-dioxane.

6. The compound of claim 1 which is c-5-(2-chlorobenzyloxy)-r-2-ethyl-c-4-methyl-1,3-dioxane.

7. An herbicidal composition comprising an herbicidally effective amount of a compound of claim 1 in admixture with an extender.

8. A method of preventing and destroying undesired plant growth which comprises applying to the locus to be protected an herbicidally effective amount of a compound of claim 1.

9. The method of claim 8 in which the undesired plant growth in *Cyperus rotundus*.

10. The method of claim 8 in which the undesired plant growth is *Setaria faberii*.

11. The method of claim 8 in which the locus to be protected is a field planted with soybeans.

12. The method of claim 8 in which the locus to be protected is a field planted with cotton.

13. The method of claim 8 in which the locus to be protected is a field planted with peanuts.

* * * * *